(12) United States Patent
Ohno et al.

(10) Patent No.: US 7,247,310 B1
(45) Date of Patent: Jul. 24, 2007

(54) TUMOR VACCINES

(75) Inventors: Tadao Ohno, Ibaraki (JP); Bao Gang Peng, Guang Shou (CN); Kam Leong, Ellicott City, MD (US); Shu Qin Liu, Ontario (CA)

(73) Assignees: Cell-Medicine, Inc., Ibaraki (JP); Riken, Saitama (JP)

( * ) Notice: Subject to any disclaimer, the term of this patent is extended or adjusted under 35 U.S.C. 154(b) by 0 days.

(21) Appl. No.: 09/890,266

(22) PCT Filed: Feb. 9, 2000

(86) PCT No.: PCT/JP00/00692

§ 371 (c)(1),
(2), (4) Date: Mar. 27, 2002

(87) PCT Pub. No.: WO00/47226

PCT Pub. Date: Aug. 17, 2000

(30) Foreign Application Priority Data

Feb. 9, 1999 (JP) ................................. 11-031197

(51) Int. Cl.
*A61K 39/00* (2006.01)
(52) U.S. Cl. .................... 424/277.1; 424/85.1
(58) Field of Classification Search ............. 424/277.1, 424/198.1, 85.2; 514/2
See application file for complete search history.

(56) References Cited

U.S. PATENT DOCUMENTS 5,861,159 A * 1/1999 Pardoll et al. ............ 424/184.1

FOREIGN PATENT DOCUMENTS

| CN | 1119459  | 3/1996  |
| CN | 00805910 | 2/2000  |
| EP | 0690125  | 11/1996 |
| WO | 90/03183 | 4/1990  |
| WO | 90/11085 | 10/1990 |
| WO | 96/01611 | 1/1996  |
| WO | 98/16238 | 4/1998  |

OTHER PUBLICATIONS

Entry of microparticle in Meririam-Webster Online downloaded on Mar. 13, 2005 from url>>www.m-w.com.*
Wordreference.com downloaded on Oct. 20, 2005, definition of homogenate.*
Definition of "particle" in Merriam-Webster Online downloaded on Oct. 26, 2005.*
Kwiatkowska et al., (1999, BioEssays, vol. 21, pp. 422-431).*
Mescher, M., and Rogers, J., J. Immunotherapy 19(2), pp. 102-112 (1996).
Golumbek, P., et al., Cancer Res. 53, pp. 5841-5844 (1993).
Pardoll, D., Nature Medicine Vacine Suppl. vol. 4, pp. 525-531 (1998).
English Language Abstract of CN 1119459.
Pardoll, D.M., Nature Med., 4 (5Suppl.), pp. 525-531 (1998).
Nestle, F.O., et al., Nature Med., 4, pp. 328-332 (1998).
Nakanishi, T., et al., Biochem. Biophys. Res. Comm., 250, pp. 793-797 (1997).
Rosenberg, S.A., et al., Nature Med., 4, pp. 321-327 (1998).
Golumbeck, P.T., et al., Cancer Res., 53, pp. 5841-5844 (1993).
Naito, M. and Seno, S., Cell Biol. International Rep., 5, pp. 675-681 (1981).
Liu, S.Q., et al., Nature Med., 2, pp. 1283-1283 (1996).
Falo, Jr., L.D., et al., Nature Med., 1, pp. 649-653 (1996).
Kim, C., et al., Cancer Immunol. Immunother., 47, pp. 90-96 (1998).
Inaba, et al., Lecture SI-3-3, Japanese Immunology Society, Dec. 2, 1998.
Guo, Y.J., et al., Nature Med., 3, pp. 451-455 (1997).
Levitsky, H.I., et al., J. Immunol., 156, pp. 3858-3865 (1996).
English Language Abstract of CN 1119459.

* cited by examiner

*Primary Examiner*—Misook Yu
(74) *Attorney, Agent, or Firm*—Greenblum & Bernstein, P.L.C.

(57) ABSTRACT

A tumor vaccine which comprises a microparticle or a lysate prepared from a solidified tumor material selected from the group consisting of a tumor tissue, a tumor cell, and a component thereof, and at least one cytokine and/or cytokine-inducing agent (e.g., a granulocyte-macrophage-colony stimulating factor and/or interleukin-2 and the like), and optionally an adjuvant. The vaccine can be easily prepared and widely applied for prevention of recurrence, inhibition of metastasis and therapeutic treatment regardless of a type of a tumor, and has excellent antitumor effect.

18 Claims, 3 Drawing Sheets

TUMOR VACCINES

The U.S. Government has a paid-up license in this invention and the right in limited circumstances to require the patent owner to license others on reasonable terms as provided for by the terms of Grant No. RO1 CA68011 awarded by The National Institutes of Health, National Cancer Institute.

TECHNICAL FIELD

The present invention relates to a tumor vaccine useful for prevention of recurrence, inhibition of metastasis and therapeutic treatment of tumors.

BACKGROUND ART

The tumor vaccine therapy is to activate immune system in vivo, particularly killer lymphocytes that play a key role in cellular immune responses, especially cytolytic T lymphocytes (hereinafter abbreviated as "CTL"), to specifically kill tumor cells without damaging normal cells, and to expect prevention of recurrence of the tumor, inhibition of metastasis, or cure of the established tumor.

Various kinds of tumor vaccines have been developed (Pardoll, D. M., Nature Med., 4(5 Suppl), pp. 525-531, 1998). Roughly tumor vaccines can be categorized depending on tumor-specific materials as follows: (1) vaccines wherein a tumor antigenic peptide with a known property is used; (2) vaccines wherein a tumor tissue extract containing an unidentified tumor antigenic peptide is used; (3) vaccines wherein the above peptide is bound to an antigen-presenting cell, especially a dendritic cell with a strong capability of antigen presentation (Nestle, F. O., et al., Nature Med., 4, pp. 328-332, 1998); (4) vaccines wherein a tumor antigenic protein is taken into a dendritic cell and loaded; (5) vaccines wherein a dendritic cell and a tumor cell are fused; (6) vaccines wherein a tumor antigen is bound to a liposome for uptake together with the liposome (Nakanishi, T., et al., Biochem. Biophys. Res. Comm., 240, pp. 793-797, 1997); (7) vaccines wherein a tumor cell, per se, is treated for inactivation with radiation or a fixing agent before administration; (8) vaccines wherein a cytokine gene, having an antigen-presenting cell stimulating effect or a lymphocyte stimulating effect, is introduced into a tumor cell and the cell is administered as a vaccine for a gene therapy, or wherein a tumor antigenic gene is introduced into a suitable cell and a tumor cell expressing the gene is administered as a vaccine; (9) vaccines wherein a tumor antigenic gene is integrated into a virus or a bacterium for infection of a patient; (10) vaccines wherein a live tumor cell, a tumor antigenic peptide or an extract of a tumor cell is administered, and separately a great amount of a cytokine is administered (Rosenberg, S. A., et al., Nature Med., 4, pp. 321-327, 1998), or wherein a cytokine is formulated into a controlled release preparation and administered (Golumbek, P. T., et al., Cancer Res., 53, pp. 5841-5844, 1993) and the like.

However, any of the above tumor vaccines is advantageous from some aspects while disadvantageous from other points of view. For example, Method (1) can only be applied to tumors which express a specific major histocompatibility complex (hereinafter abbreviated as "MHC", and for Class I referred to as "MHC-I" and for Class II as "MHC-II") that meets to an identified tumor antigenic peptide. The human MHC is highly diverse, and consequently, clinical cases are very limited in which those tumor antigenic peptides can meet the MHC. To overcome the problem, Method (2) using a tumor tissue extract containing an unidentified tumor antigenic peptide has been developed. However, only a trace amount of the tumor antigenic peptide can be extracted from tumor tissues, and it is often impossible to concentrate the extract when the amount of the tumor as a raw material is small. Therefore, the extract cannot be administered in a large amount such as identified and synthesized tumor antigen peptides, and effects are limited.

Where a tumor antigenic peptide is bound to an antigen-presenting cell beforehand, such as in Method (3), a high CTL activating effect is obtained. However, peripheral blood or bone marrow for isolation and preparation of the antigen-presenting cell, especially a dendritic cell having strong antigen presenting capability, should be derived from the patient who bears the tumor and is to be applied with the tumor vaccine therapy to prevent dangerous graft-versus-host-disease (hereinafter abbreviated to "GVHD"), which requires a highly skilled technique and is complicated. Methods (4) and (5) have the same problem as that of Method (3), and in addition, a fusion process is very complicated in Method (5). Although there is no concern about the risk of GVHD in Method (6), an efficiency of the introduction of the tumor antigen into the antigen-presenting cell is sometimes not successfully high, and a relatively great amount of the tumor antigen is required to prepare the tumor vaccine.

Method (7) is also complicated and costly because the tumor cells are obtained by mass culture, and moreover, the method has a problem in that the amount of the tumor antigen contained in the tumor cells per se is very small. This method is known to be successful in tumor cells with high antigenicity when treatment with poly(L-lysine) is applied (Naito, M. and Seno, S., Cell Biol. International Rep., 5, pp. 675-681, 1981). However, the method remains unsuccessful in tumor cells with low antigenicity. Genetic therapies of Methods (8) and (9) are extraordinarily complicated in procedures to obtain approval for the treatment, as well as in therapeutic operations. Method (10) is promising at present; however, especially in the method of Rosenberg et al., a huge amount of interleukin-2 simultaneously administered causes a severe side effect, and clinical results for tumors treatment are sometimes not satisfactory. Even when cytokines are formulated as controlled release preparations by the method of Golumbek et al., a complication still remains in preparation of X-ray-irradiated live tumor cells.

The tumor vaccine is desirably provided in a form that can be handled as easily as possible. From this point of view, methods involving administration of live tumor cells or antigen-presenting cells as a part of a tumor vaccine have problems in that they are technically very complicated as operations under a live state are required. The operations are further complicated for a genetic therapy. When tumor antigenic peptides are known, the peptides can be synthesized in large quantities for administration. However, there are a large variety of tumor antigenic peptides, and additionally, due to restriction from MHC molecules of a patient individual, it often cannot be appropriately determine which of tumor antigenic peptides is applicable to the patient individual, which may limit the application. When a tumor antigenic protein is used instead of the tumor antigenic peptide, the protein is processed in the antigen-presenting cells and then a tumor antigenic peptide that meets the MHC is selected. Accordingly, the method is not restricted by the MHC of a patient individual to be treated. However, this method has a problem in that purification and large-scale preparation of the tumor antigenic protein, per se, is difficult.

As a method for inducing CTL, a method is known in which CTL is induced from peripheral blood mononuclear cells on a fixed tumor tissue obtained by removing paraffin from pathological sections (Liu, S. Q. et al., Nature Med., 2, pp. 1283-1283, 1996). Generally, when an antigenic protein in a soluble state is provided to antigen-presenting cells, the protein has a high stimulating effect on liquid immunity that links to production of antibodies by binding antigenic proteins-derived antigen peptides to MHC-II, whereas the protein has a low stimulating effect on cellular immunity that activates killer cells by binding antigenic proteins-derived antigen peptides to MHC-I. Falo et al. conducted induction of CTL that react to ovalbumin-derived antigenic peptides by binding ovalbumin as a foreign protein with strong antigenicity to iron powder and administering the product to mice without addition of an adjuvant (Falo, Jr., L. D., et al., Nat. Med., 1, pp. 649-653, 1995).

The inventors of the present invention found that CTL can be induced efficiently from peripheral blood lymphocytes of the same individual by fixing soluble tumor antigenic proteins on fine polystyrene beads and subjected the product as fine solids to phagocytosis by antigen-presenting cells in human peripheral blood mononuclear cells in a cell culture system in vitro (Kim, C., et al., Cancer Immunol. Immunother., 47, pp. 90-96, 1998). It is also known that dead cell-derived antigens can efficiently induce immune responses thousands folds stronger when the antigens are phagocytosed in the state of dead cells by immature dendritic cells than when the antigens are not phagocytosed (Inaba, et al., Lecture SI-3-3, Japanese Immunology Society, Dec. 2, 1998).

DISCLOSURE OF THE INVENTION

An object of the present invention is to provide a tumor vaccine which can be simply handled, generally applied for prevention of tumor recurrence, inhibition of metastasis and therapeutic treatment, regardless of a type of a tumor, and also has a strong antitumor effect.

The inventors of the present invention conducted intensive studies to achieve the foregoing object. As a result, they found that the prevention of tumor recurrence, inhibition of metastasis, and therapeutic treatment can be achieved with high efficiency by using a material solidified from tumor tissues, tumor cells, or components thereof by a fixation operation, and processing the material into microparticles in a size that can be phagocytosed by antigen-presenting cells, or lysing the material by a lysation operation, and then using the resulting product as a tumor vaccine in combination with at least one kind of cytokines.

The present invention thus provides a tumor vaccine which comprises microparticles prepared from a solidified tumor material selected from the group consisting of tumor tissues, tumor cells and components thereof, and at least one kind of cytokines and/or cytokine-inducing agents; and a tumor vaccine which comprises a lysate prepared from a solidified tumor material selected from the group consisting of tumor tissues, tumor cells and components thereof, and at least one kind of cytokines and/or cytokine-inducing agents.

According to preferred embodiments of the present invention, provided are the aforementioned tumor vaccine which further contains an adjuvant unspecifically inducing immune responses; the aforementioned tumor vaccine for administration to an identical site in vivo; the aforementioned tumor vaccine which contains a cytokine-controlled release preparation as the cytokine; and the aforementioned tumor vaccine which contains a granulocyte-macrophage-colony stimulating factor and/or interleukin-2 as the cytokine. From another aspect, there is provided a tumor vaccine for using in combination with at least one kind of cytokines which contains, as an active ingredient, microparticles prepared from a solidified tumor material selected from the group consisting of tumor tissues, tumor cells and components thereof, or a lysate prepared from the tumor material.

From still other aspects, there are provided a method of therapeutic treatment of, prevention of recurrence of, and inhibition of metastasis of a tumor which comprises the step of administering an effective amount of microparticles prepared from a solidified tumor material selected from the group consisting of tumor tissues, tumor cells and components thereof, and at least one kind of cytokines and/or cytokine-inducing agents; a method which comprises the step of administering an effective amounts of a lysate prepared from a solidified tumor material selected from the group consisting of tumor tissues, tumor cells and components thereof, and at least one kind of cytokines and/or cytokine-inducing agents; the aforementioned methods in which the administration is repeatedly made an identical site; and a use of the microparticles or the lysate prepared from the aforementioned solidified tumor material for the manufacture of the aforementioned tumor vaccines.

BEST MODE FOR CARRYING OUT THE INVENTION

Figure 1:
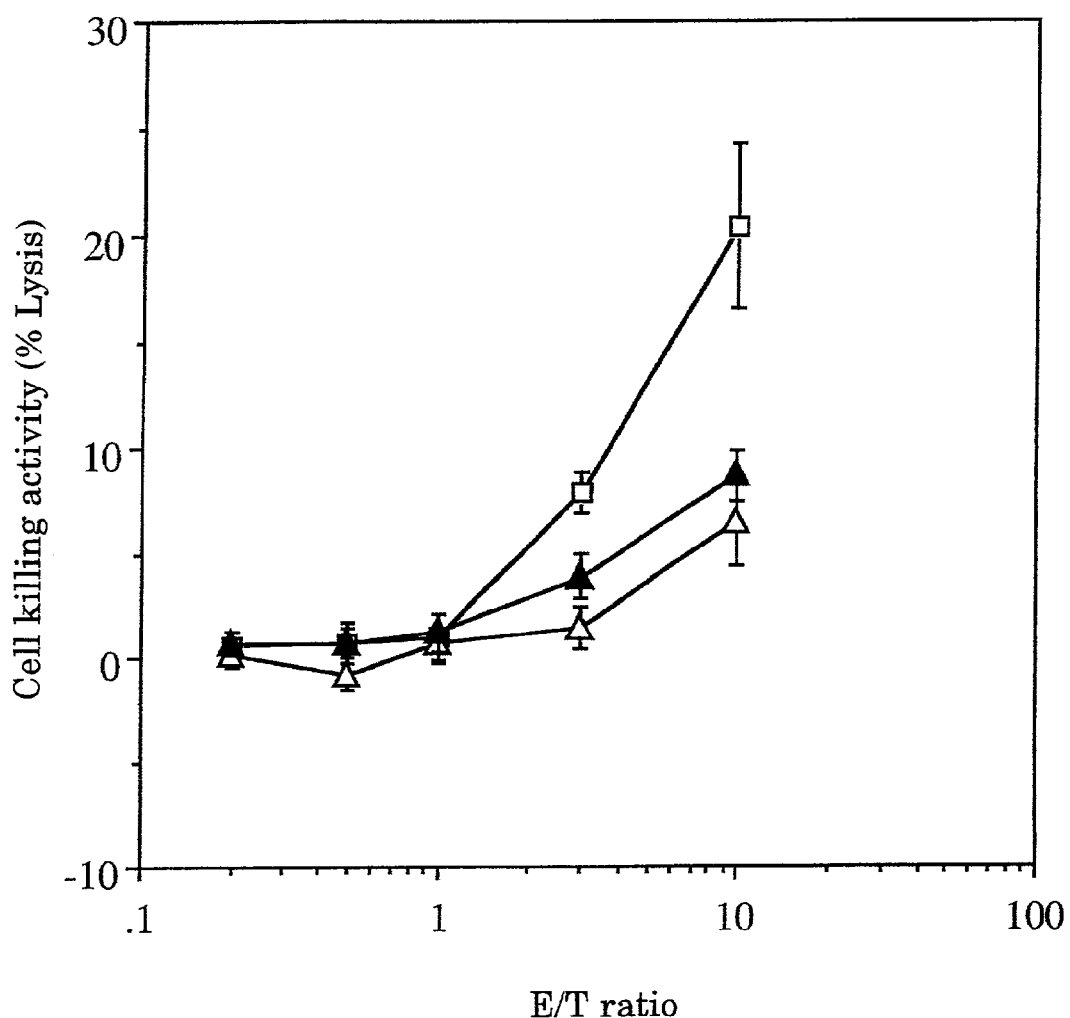
FIG. 1 shows the CTL activity induced by in vitro sensitization using the tumor vaccine of the present invention. In the figure, % Lysis of the vertical axis shows the killing activity by CTL against the target cells, and E/T ratio of the horizontal axis shows the ratio of the CTL number and the target cell number at the killing activity measurement by the 4 hour Cr-51 release method. □ shows C16-F10; Δ Hepa 1-6; and ▲ Lewis lung carcinoma.

The tumor vaccine of the present invention is characterized to comprise microparticles or a lysate prepared from a solidified tumor material selected from the group consisting of tumor tissues, tumor cells and components thereof as a tumor antigen, and further containing at least one kind of cytokines and/or cytokine-inducing agents.

As the tumor cells or tumor tissues, for example, those derived from a mammal, preferably those derived from a human, can be used. Those from any species of organisms may be used so far that the cells or tissues contain a tumor antigen of a tumor to be therapeutically or preventively treated. The types of the tumor tissues are not particularly limited so far that they contain tumor cells. When components of tumor cells or tumor tissues are used, the types of the components are not limited so far that they contain a substance as potential tumor antigen. Fresh specimens such as solid cancer tissues, bone marrow, and white blood cells which contain cancer cells isolated or collected from the living body can be used as tumor materials. As the component of tumor tissues or tumor cells, for example, antigenic peptides or antigenic proteins can be used.

The fixation method to prepare the solidified tumor material is not particularly limited, and any means available to those skilled in the art may be applied. For example, when a tissue fixing agent is used, neutral formalin, glutaraldehyde, an alcohol such as methanol and ethanol and the like can be used. Besides the aforementioned methods, any method may be used so far that fresh tissues or cells or components thereof can be solidified. Tumor materials may be solidified by a method such as paraffin embedding, freezing and the like. When tissues originally in a solid state such as bone tissues are used as the solidified tumor material, it is preferably to apply an appropriate fixation method.

The preparation method of microparticles is not particularly limited, and applicable methods include, for example, a method of grinding the solidified tumor tissues to prepare microparticles of fine fragments, as well as a method of lysing ground fragments of tumor tissues or tumor cells to fix the lysate to solid microparticles, a method of fixing soluble tumor antigens such as antigenic peptides and antigenic proteins to solid microparticles and the like. As the solid microparticles, for example, iron powder, carbon powder, polystyrene beads and the like from about 0.05 to 1,000 μm in diameter can be used. Usable microparticles include ground tissue fragments, tumor cells or soluble tumor antigens bound to lipid particles such as liposomes so as to be recognized as microparticles by the antigen-presenting cells to allow phagocytosis, or a microparticles obtained by binding soluble tumor antigens, per se, to each other by using a binder or a crosslinking agent.

Sizes of microparticles are not especially limited, however, a size that allows phagocytosis by cells with phagocytic ability in vivo is desirable. It is not necessary to grind fixed tumor cells that are originally in a state of small single cells. However, it is desirable to apply grinding or dispersing treatment when the cells aggregate during the fixation operation. For the grinding or dispersing treatment, treatment with a homogenizer, ultrasonic treatment, partial digestion with a digestive enzyme and the like can be used. The microparticles can also be prepared by passing through a screen having a pore size of not more than 1,000 μm, preferably not more than 380 μm. The preparation of these microparticles is well known to those skilled in the art, and the skilled artisan can prepare the microparticles by a single appropriate method or a combination of plural methods.

As a method to prepare the lysate from solidified tumor materials, for example, a method using a proteolytic enzyme can be applied. An example of the proteolytic enzyme includes proteinase K. A method employing an appropriate combination of an enzyme other than the proteolytic enzyme, an acid, an alkali and the like may also be utilized. Any method that can achieve lysis of the solidified tumor material may be employed, and those skilled in the art can choose an appropriate method. The lysate may be fixed to the solid microparticles mentioned above.

The term "lysate" used in the specification means a state of dispersion of the solidified tumor material in an aqueous medium such as water, physiological saline, and a buffer solution to an extent that any solid mass cannot be observed with naked eyes, and to an extent that the dispersoids can be phagocytosed by the antigen-presenting cells. However, the term should not be construed in any limiting way. The details of the preparations of the fixed tumor materials, the preparations of the microparticles, and the preparations of lysates are specifically described in the examples of the present specification. Accordingly, those skilled in the art can prepare the desired microparticles or the lysates by referring to the above general explanations and specific explanations in the examples, and appropriately modifying or altering those methods, if necessary.

The type of cytokines contained in the tumor vaccine of the present invention is not especially limited, and one or more kinds of cytokines can be used. For example, granulocyte-macrophage-colony-stimulating factor (hereinafter abbreviated as "GM-CSF"), or interleukin-2 (hereinafter abbreviated as "IL-2") may preferably be used, and a combination of GM-CSF and IL-2 may also preferably be used. In addition, other cytokines or cytokine-inducing agents can be used which stimulate the local immune cells in vivo, and consequently achieve the same conditions as those achieved by GM-CSF and/or IL-2 administration. As cytokines or cytokine-inducing agents besides these two kinds of cytokines, examples include interleukin-12, interleukin-18, interferon category and the like. However, cytokines or cytokine-inducing agents are not limited to these examples.

These cytokines or inducing agents may preferably be prepared as controlled-release preparations so that concentrations at sites received administration can be kept at a high level as long as possible. Such means for preparing controlled-release preparations is, for example, reported by Golumbek et al (Golumbek, P. T., et al., Cancer Res., 53, pp. 5841-5844, 1993). Various methods for preparation of controlled release preparations are known in the field of the art, and any method can be applied.

The tumor vaccine of the present invention may contain an adjuvant that induces non-specific immune responses. The adjuvant can be used alone or in combination of two or more kinds. As the adjuvant, examples include Freund complete adjuvant, Freund incomplete adjuvant, bacterial preparations such as BCG, bacterial component preparations such as tuberculin, natural macromolecular substances such as keyhole limpet hemocyanine and yeast mannan, Alum, synthetic adjuvant preparations such as Titer Max Gold and the like. However, the adjuvants are not limited to these specific examples, and any substances may be used so far that they are effective as adjuvants. Whether an adjuvant should be used or not can be judged by intensity of inflammatory reaction at a site of administration or intensity of antitumor effect induced as a result of the administration as a standard. For example, alternate administrations of the tumor vaccine containing an adjuvant and the vaccine without adjuvant can be applied to the same site.

Forms of preparation of the tumor vaccine of the present invention are not particularly limited, and desirably, the forms of preparation may be suitable for local administration. The methods for manufacturing pharmaceutical preparations are not particularly limited, and a preparation in a desired form can be prepared by applying a single method available in the field of the art or methods in an appropriate combination. For the manufacture of pharmaceutical preparations, aqueous media such as distilled water for injection and physiological saline, as well as one or more kinds of pharmaceutical additives available in the field of the art can be used. For example, buffering agents, pH adjusting agents, solubilizing aids, stabilizing agents, soothing agents, antiseptics and the like can be used, and specific ingredients thereof are well known to those skilled in the art. The tumor vaccine can also be prepared as a solid preparation such as a lyophilized preparation, and then prepared as an injection by adding a solubilizing agent such as distilled water for injection before use.

When vaccine therapy is carried out using the tumor vaccine of the present invention, the tumor vaccine may be administered only once. However, it is desirable to repeat the administration to the same site of a body to achieve coexistence of a tumor antigen and a cytokine or a cytokine-inducing agent as long as possible. For example, both components may preferably coexist for 3 hours or more so that inflammatory reaction at the site of administration can be induced and conditions can be achieved wherein immune cells are concentrated and cells are kept at the site. When a tumor vaccine without adjuvant is administered, an adjuvant may be administered to the same site. Generally, the tumor vaccine can be administered to a patient from which the tumor material is derived; however, the vaccine can also be administered to a patient bearing a tumor that contains, from a viewpoint of pathological diagnosis, the same or relative species of a tumor antigen as that contained in the tumor material.

The site to be administered is not particularly limited. Preferred sites include those where cytokines are hardly be diffused and disappeared, for example, intradermal, subcutaneous or intramuscular sites, in lymphnodes, and in a main organ such as spleen. However, by choosing a dosage form which prevents ready diffusion of the active ingredients of the tumor vaccine, local administrations may sometimes be performable to any site of a body, or by applying a drug delivery system, the systemic administration may sometimes be possible. The dose and administration period of the tumor vaccine of the present invention are not particularly limited. It is desirable to determine an appropriate dose and administration period by observing effects of the vaccine therapy. The administration can be made, for example, by injections and the like.

EXAMPLES

The present invention will be explained more specifically with reference to the examples. However, the scope of the present invention is not limited to the following examples.

Example 1

The Action of Tumor Vaccine of the Present Invention

Using syngeneic transplanted mouse hepatoma with well-known low antigenicity (Guo, Y. J., et al., Nat. Med. 3:451-5, 1997) as the target, the tumor vaccine of the combination of fixed tumor cells as tumor antigens, GM-CSF, IL-2 and an adjuvant was investigated to see whether or not the vaccine inhibited the hepatoma formation.

[Method]

1. Fixed Tumor Cells

Hepatoma cells Hepa 1-6 developed in C57BL/6 (obtained from The Cell Bank of The Institute of Physical and Chemical Research) were cultured and fixed with 3% paraformaldehyde in Dalbecco's phosphate buffered saline (hereinafter abbreviated as "PBS") for 2 hours. The fixed cells were washed once with 70% alcohol for sterilization and aseptically washed four times with PBS, then added with the Dulbecco's minimum essential medium (hereinafter abbreviated as "DMEM") containing 10% fetal bovine serum, and incubated in a carbon dioxide gas incubator at 37° C. for 2 days. After the medium was removed, the cell layer was added with an aqueous solution of poly-L-lysine (50 μg/ml), allowed to stand at room temperature for 2 hours, and then washed four times with PBS. Then, the cells were collected with a scraper and diluted with PBS to $1.25 \times 10^8$ cells/ml. Any of the fixed Hepa 1-6 cells had a size of 100 μm or less which enabled phagocytosis by antigen-presenting cells with phagocytic ability.

2. Preparation of Cytokine Microspheres

As a cytokine to be prepared into microspheres, mouse GM-CSF or human IL-2 (both Immunex) was used. A human serum albumin injection solution (25% concentration, Albuminar-25, Centeon L.L.C., Illinois, USA) was diluted with water distilled twice to 5%, and adjusted to pH 3.0 with hydrochloric acid. The solution was further diluted to 2.5%, and then passed through a filter having the pore size of 0.22 μm for sterilization. To a 5 ml centrifugation tube, 100 μg of GM-CSF or $10^6$ IU of IL-2 was added, then 1 ml of a heparin solution for injection (commercially available for hospital, 1,000 U/ml, Elkins-SINN, Inc., NJ, USA) was placed, and 1 ml of the aforementioned 2.5% human serum albumin injection solution (pH 3.0) was added with stirring by a voltex mixer. After the stirring was continued for 30 seconds or more, the formed microparticles were recovered by centrifugation. The encapsulation efficiency was calculated from the supernatant.

The pellets of microparticles were suspended in 2 ml of water distilled twice, and added with a solution of 1-ethyl-3-(3-dimethylaminopropyl)carbodiimide (hereinafter abbreviated as "EDC") at a concentration of 20 mg/ml, which was passed beforehand through a filter having the pore size of 0.22 μm for sterilization, to adjust the concentration to 0.8 mg/ml. The mixture was stored at 25° C. for 15 minutes, and added with 2 ml of aseptic 0.1 M glycine solution. After the solution was stored at 25° C. for 30 minutes, the resulting suspension generating stable microspheres was centrifuged by a horizontal rotor having the radius of 12 cm at 2,000 rpm for 10 minutes to precipitate and collect the microspheres. The microspheres were washed 6 times in total by repeating the operations of adding with an appropriate amount of twice-distilled water, suspending, and centrifuging. Then the microparticles were suspended in physiological saline so as to contain 1 μg of GM-CSF (corresponding to $10^6$ IU) or $10^3$ IU of IL-2 in 20 μl of the suspension.

3. Determination of Sensitization and Tumor Rejection Reaction

The fixed Hepa 1-6 cells prepared in the above Experiment 1, the GM-CSF microspheres and IL-2 microspheres prepared in the above Experiment 2, and Titer Max Gold (CytRX, Atlanta, Norcross, Ga.) commercially available as an adjuvant were mixed to give a tumor vaccine. Each amount was $1.25 \times 10^6$ cells, $10^6$ U, $10^3$ IU, and 20 μl in order based on 0.5 ml of the tumor vaccine. Tumor vaccines having different combinations of these constituting preparations were also prepared. The combinations are described in Tables 1, 2 and 3.

The tumor vaccine was intradermally injected to the root of the tail of each male C57BL/6 mice of 6 to 8 weeks old which were syngeneic to Hepa 1-6 cells in an amount of 0.05 ml per mouse. One group consisted of 5 mice. The control group of 5 male C57BL/6 mice was injected with 0.05 ml of PBS. After 7 days, this administration was made once again to the same site, and after another 7 days, $10^7$ cultured live Hepa 1-6 cells suspended in 0.05 ml of PBS were directly injected to the liver (subcapsule of the maximum hepatic lobule). After 21 days, the size of the formed hepatoma tissue was measured to calculate the volume.

[Results]

As shown in Table 1, all the mice in the control group formed hepatoma, and the mean volume of the cancer tissue was 270 mm$^3$. Whilst no tumor was observed in 4 mice in 5 in the group treated with the tumor vaccine containing the fixed Hepa 1-6 cells, Titer Max Gold of the adjuvant, the IL-2 microspheres and the GM-CSF microspheres (represented as the ratio of tumor-free mice in the table), and one mouse in which hepatoma was observed formed a small tumor of only 18 mm$^3$. The effects of the vaccine therapy for the tumor were clearly demonstrated.

TABLE 1

| Sensitization | Ratio of tumor-free mice | Tumor volume (mm$^3$) (Mean ± SD) | Range |
|---|---|---|---|
| Control group | | | |
| (A) PBS | 0/5 | 270 ± 146 | 140-480 |
| Treated group | | | |
| (B) Fixed Hepa 1-6 cells + Titer Max Gold + IL-2/GM-CSF microspheres | 4/5 | 3.6 ± 8 | 0-18 |

To judge the importance of the combination of the constituting components of the tumor vaccine, the tumor vaccine components were varied in the treated groups. The results are shown in Table 2. A similar results to those in Table 1 were obtained in the control group (A) and the treated group (E), which shows reproducibility.

TABLE 2

| Sensitization | Ratio of tumor-free mice | Tumor volume (mm$^3$) (Mean ± SD) | Range |
|---|---|---|---|
| Control group | | | |
| (A) PBS | 0/5 | 420 ± 326 | 144-910 |
| Treated group | | | |
| (B) PBS + Fixed Hepa 1-6 cells + Titer Max Gold | 0/5 | 152 ± 106 | 75-294 |
| (C) PBS + Fixed Hepa 1-6 cells + Titer Max Gold + IL-2 microspheres | 0/5 | 67 ± 97 | 18-240 |
| (D) PBS + Fixed Hepa 1-6 cells + Titer Max Gold + GM-CSF microspheres | 2/5 | 32 ± 43 | 0-105 |
| (E) Fixed Hepa 1-6 cells + Titer Max Gold + IL-2/GM-CSF microspheres | 4/5 | 3.6 ± 8 | 0-18 |

In this table, the mice were sensitized with the tumor vaccine containing only the fixed Hepa 1-6 cells and the adjuvant Titer Max Gold in the treated group (B), and no tumor-free mouse was observed in the group. Accordingly, the importance of the cytokine to be used in combination was clearly demonstrated. In the treated group (C), the tumor vaccine containing only the IL-2 microspheres in addition to the fixed Hepa 1-6 cells and the adjuvant Titer Max Gold was used. Similarly, no tumor-free mouse was observed. However, the size of developed tumors was apparently small on the whole, and the mean tumor volume was 67 mm$^3$, which was only ⅙ of those developed in the treated group (A). Accordingly, the importance of the IL-2 microspheres was demonstrated. In the treated group (D), the tumor vaccine containing only the GM-CSF microspheres in addition to the fixed Hepa 1-6 cells and the adjuvant Titer Max Gold was used, which gave two tumor-free mice. Accordingly, the importance of the GM-CSF microspheres was demonstrated. However, the number of tumor-free mice was only half of that in the treated group (E), and the result was inferior to the treated group (E). From these results, it was revealed that the combination of the cytokines of IL-2 and GM-CSF was most important.

Moreover, in order to investigate the necessity of the fixed tumor cells as tumor antigens and calculate the effects of adjuvants, a tumor vaccine without the fixed tumor cells, or a tumor vaccine without adjuvant was prepared, and effects were compared. The results are shown in Table 3.

TABLE 3

| Sensitization | Ratio of tumor-free mice | Tumor volume (mm$^3$) (Mean ± SD) | Range |
|---|---|---|---|
| Control group | | | |
| (A) PBS | 0/5 | 231 ± 146 | 120-480 |
| Treated group | | | |
| (B) PBS + Titer Max Gold | 0/5 | 174 ± 149 | 60-432 |
| (C) PBS + Titer Max Gold + IL-2/GM-CSF microspheres | 0/5 | 300 ± 258 | 60-648 |
| (D) PBS + IL-2/GM-CSF microspheres | 0/5 | 210 ± 170 | 60-480 |
| (E) PBS + Fixed Hepa 1-6 cells | 1/5 | 85 ± 78 | 0-210 |
| (F) PBS + Fixed Hepa 1-6 cells + Titer Max Gold | 1/5 | 78 ± 58 | 0-150 |
| (G) Fixed Hepa 1-6 cells + Titer Max Gold + IL-2/GM-CSF microspheres | 5/5 | 0 | 0 |
| (H) PBS + Fixed Hepa 1-6 cells + IL-2/GM-CSF microspheres | 4/5 | 7 ± 16 | 0-36 |

The control group (A) and the treated group (G), which were the same as those in Table 1, gave similar results to those shown in Table 1. However, all the five mice in the treated group (G) were tumor-free. In the treated group (C) in which the mice were treated with the tumor vaccine without the fixed Hepa 1-6 cells but, as in the treated group (G), containing the IL-2 microspheres, the GM-CSF microspheres and the adjuvant Titer Max Gold, development of large hepatoma (average 300 mm$^3$) was observed in all the mice. From these results, it was revealed that tumor antigens of solid microparticles are extremely important. In fact, as shown in the treated group (E), one mouse was tumor-free even by using the tumor vaccine obtained by adding only fixed Hepa 1-6 cells to PBS. In contrast, in the treated group (H) using the tumor vaccine containing the fixed Hepa 1-6 cells, the IL-2 microspheres and the GM-CSF microspheres but without the adjuvant Titer Max Gold, ⅘ mice were tumor-free. However, one mouse developed a small but clear hepatoma of 36 mm³. Accordingly, it was revealed that the effect of an adjuvant which induces unspecific immune responses was worth being considered.

From these results, it was concluded that, as a tumor vaccine to suppress cancer tissue formation of mouse hepatoma by Hepa 1-6 cells, the combination of the fixed Hepa 1-6 cells, the IL-2 microspheres, the GM-CSF microspheres and the adjuvant Titer Max Gold was most effective to exhibit the antitumor effect.

Example 2

Method for Preparation of Microparticulate Tumor Antigens from Fixed Tumor Tissues Fixed tumor tissues containing fixed tumor cells were ground to prepare fine solidified tumor antigens.

[Method]

The Hepa 1-6 cells used for the mice in the control group (A) in Example 1 were subcutaneously transplanted in the same amount to the mouse thigh, and the developed hepatoma tissue was isolated after 3 weeks and fixed by soaking in a commercially available neutral formalin solution at room temperature for 3 days. The tissue was taken out, cut with ophthalmic scissors into a fine mince having the diameter of about 1 mm, added with PBS in 10 times amount of the original hepatoma wet weight, and homogenized with ice cooling by a homogenizer (Heidorf Co., DIAX-600, 6G Generator shaft) for 30 seconds. The homogenization was repeated 5 times with intervals of 3 minutes or more for ice cooling. 1.2 ml of the homogenate was placed in a 1.5 m Eppendorf centrifugation tube, and centrifuged by an Eppendorf high performance microcentrifugator at 15,000 rpm for 3 minutes, and the packed volume was measured. The measurement was carried out by comparing a 1.5 ml Eppendorf centrifugation tube filled with 50 μl or more of water. The residual homogenate was centrifuged by a horizontal rotor having the radius of 12 cm at 2,000 rpm for 10 minutes to obtain the precipitate.

This precipitate was suspended in 5 ml of 70% alcohol for washing, centrifuged at 2,000 rpm for 10 minutes to remove the supernatant, and suspended again in PBS of the original volume. The suspension was passed through a stainless screen of 40 mesh (Sigma, S0770, pore size 380 μm). 1.2 ml of the passed suspension was placed in a 1.5 ml Eppendorf centrifugation tube and centrifuged by a high performance microcentrifugator at 15,000 rpm for 3 minutes, and the packed volume was measured. The measurement was carried out by comparing a 1.5 ml Eppendorf centrifugation tube filled with a given amount of water.

[Results]

The tissue fragments in the homogenate obtained from the fixed hepatoma tissues were very fine so as to easily pass a fine injection needle of the common 22G standard or less after the pass through the aforementioned mesh. The number of the recovered cells was unknown; however, the recovered packed volume was apparently over the volume corresponding to $10^7$ live Hepa 1-6 cells by visual observation, and the recovery measured by the packed volume before and after the pass of the aforementioned mesh was 78%. The homogenate contains solidified tumor cell fragments in a sufficient amount that is required by a tumor vaccine, and accordingly, the homogenate can be used as microparticulate tumor antigen.

Example 3

Antitumor Effect of CTL Induced In Vitro

The tumor cell killing activity and the specificity were investigated when CTL was induced using fixed tumor cells as a target.

[Method]

1. Fixed Tumor Cells $10^8$ to $10^9$ cells of substrains B16-F10 of melanoma cell B16 developed by C57BL/6 mice (obtained from American Type Culture Collection, Bethesda, Mass., USA) were soaked in 10% formalin solution and fixed at 4° C. for 2 to 4 weeks. The resultant was suspended in 30 ml of 70% ethanol, washed by centrifugation, and further suspended in PBS and washed by centrifugation 3 times. The resultant was suspended in an appropriate amount of the MEM medium for cell culture containing 10% fetal bovine serum, and warmed to 37° C. for 2 to 3 days or to 60° C. for 4 hours. Then the resulting cells were recovered by centrifugation (hereinafter the cells subjected to this treatment are referred to as "fixed B16-F10 cells") and suspended to adjust to $5 \times 10^8$ cells/ml.

2. Determination of Antitumor Effect by In Vitro Sensitization and Tumor Cell Killing Activity From the spleen of C57BL/6 mice without any sensitization, spleen cells were obtained by lightly crushing the tissues in the manner well known to those skilled in the art. Most of them are lymphocytes. $4 \times 10^7$ cells of them were taken and proliferated by culturing together with $2 \times 10^6$ fixed B16-F10 cells in the RPMI-1640 medium containing 10% fetal bovine serum added with human IL-1β (167 U/ml), human IL-2 (67 IU/ml) and human IL-6 (134 U/ml) (Immunex, respectively) for 10 days. The entire culture solution was changed at the 3rd and 5th day after the start of the culture, and then the half of the solution was changed every 3 days. The lymphocytes proliferated in this way were used as CTL.

For the determination of the antitumor effect, tumor cell killing activity of CTL was measured in vitro. The cell killing activity was measured by the 4 hour Cr-51 release method widely known as a standard measuring method using live B16-F10 cells without irradiation as the target cells. In addition, Hepa 1-6 cells described in Example 1 and Lewis lung carcinoma cells obtained from America Type Culture Collection (Bethesda, Mass., USA) were used in place of the B16-F10 cells as the target cells for comparison.

[Results]

FIG. 1 shows the CTL activity induced by the vitro sensitization. % Lysis of the vertical axis represents the killing activity of the target cells by CTL, and E/T ratio of the horizontal axis is the ratio of the CTL number and the target cell number at the killing activity measurement by the 4 hour Cr-51 release method. When the B16-F10 cells were used as the target (□), E/T ratio was 10 and about 20% was killed. This activity was apparently higher than those when other two kinds of the tumor cells derived from the same C37BL/6 mouse were used as targets. These results suggest that the CTL induced against the fixed B16-F10 cells has ability to recognize and kill live B16-F10 cells more specifically than the other two kinds of tumor cells, although the CTL is derived from the same C57BL6 mouse.

Example 4

Method for Preparation of Microparticulate Tumor Antigens from Solubilized Fixed-Tumor Cells and In Vivo Antitumor Effect Thereof

When a pathological section is used as a material, an yield may sometimes be poor in preparation of microparticles according to the method shown in Example 2, and as a result, preparation of tumor vaccines may sometimes be difficult. In such cases, tumor vaccines can be prepared by lysing fixed tumor cells with a digestive enzyme and formulated as a microsphere preparation, and then combining the resultant with another microsphere preparation of a cytokine.

[Method]

1. Method for Preparation of Solubilized Fixed-Tumor Microspheres and Method for Preparation of Tumor Vaccine Preparations The fixed B16-F10 cells were suspended in PBS to adjust to $5\times10^8$ cells/ml. The suspension was added with pronase K (Sigma) to adjust to 1 mg/ml, and warmed to 56° C. overnight. The precipitate was removed by centrifugation at 3,000 rpm for 10 minutes, and the supernatant was used as the solubilized B16-F10 antigen. This supernatant was added with the human serum albumin injection solution used in Example 1 to adjust the final albumin concentration to 2.5%. The procedures after the above treatment were the same as those for preparation of GM-CSF microspheres in Example 1, and thus soluble fixed tumor microspheres were prepared. The resultant was diluted so that the amount of tumor antigen, contained in the microspheres which were suspended in 80 µl of physiological saline, finally corresponded to $10^7$ tumor cells. The resultant was mixed with 20 µl of the GM-CSF microspheres prepared by the same manner as in Example 1 to give a tumor vaccine preparation.

2. Determination of Antitumor Effect by In Vivo Sensitization and Tumor Cell Challenge Male C57BL/6 mice of 6 to 8 weeks old (10 mice a group) which were syngeneic to B16-F10 cells were anesthetized with ether, and the tumor vaccine preparation was subcutaneously injected to the thigh in an amount of 100 µl per mouse. The control group was injected with the same amount of PBS. When the administration of the tumor vaccine was repeated, the administration in the same amount was repeated every other week. Two weeks after the initial administration of the tumor vaccine, $10^5$ cultured live B16-F10 cells suspended were subcutaneously injected to the abdomen. The antitumor effect was calculated as a percentage of remaining tumor-free mice.

[Results]

Figure 2:
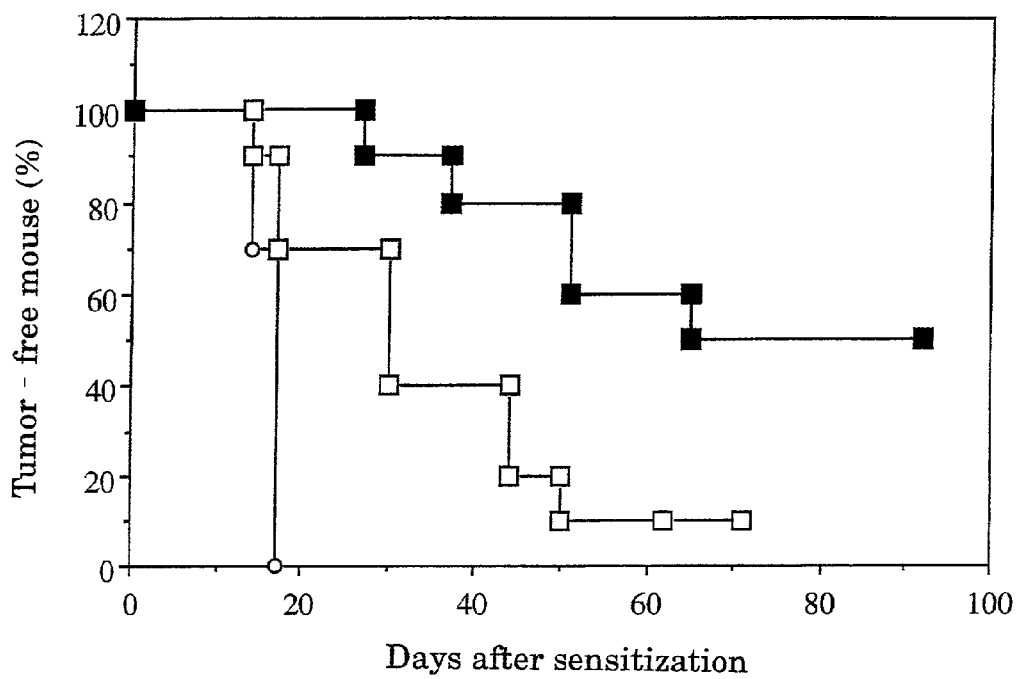
FIG. 2 shows the result of the in vivo sensitization experiment with the tumor vaccine prepared by using soluble fixed tumor cells in Example 4. In the figure, ○ shows the PBS control group; □ the group administered once with the tumor vaccine; and ■ the group administered 3 times with the tumor vaccine.

FIG. 2 shows the result of the in vivo sensitization experiment. As compared to the control group, the remaining tumor-free mice in the groups administered with the tumor vaccine preparation exhibited apparently higher percentages. Particularly in the group administered with the tumor vaccine preparation 3 times, half of the mice still maintained the tumor-free condition over 90 days of the observation period. These results suggest that the CTL against B16-F10 cells was induced by the tumor vaccine administration in vivo, and therefore, live B16-F10 cells injected afterward were killed and the cells did not live and grow in the half of the mice. In addition, these results suggest that the tumor vaccine therapy which successfully prevents recurrence of a tumor can be established by preparing a tumor vaccine preparation using an isolated tumor cells after an extirpation operation of the tumor.

Example 5

CTL Inducing Effect of Tumor Vaccine Preparation Prepared from Solubilized Fixed-Tumor Cells

[Methods]

Used were male C57BL/6 mice administered with the tumor vaccine preparation in the same manner as in Example 4, mice of the control group, and mice as another control group administered with a mixture of $10^7$ live B16-F10 cells irradiated beforehand by 50 Gy of X-ray and 20 µl of the GM-CSF microspheres as the control tumor vaccine preparation in place of the group administered once with the tumor vaccine preparation in Example 4. The spleen and inguinal lymph node were isolated from these mice and the tissues were lightly crushed to obtain lymphocytes. These lymphocytes were proliferated by culturing for 7 days in the RPMI-1640 medium containing 10% fetal bovine serum added with human IL-1β (167 U/ml), human IL-2 (67 IU/ml) and human IL-6 (134 U/ml) (all from Immunex). This experiment system is different from the system according to Example 3 in that no stimulation by the fixed B16-F10 cells was applied during the culturing period. The system ensures no possibility of CTL induction during the culturing period and it can be expected that CTL proliferates in vitro in the number proportional to that of the CTL induced in vivo. The cell killing activity of the cultured lymphocytes was measured by the 4 hour Cr-51 release method widely known as a standard measuring method using live B16-F10 cells without irradiation as the target cells.

[Results]

Figure 3:
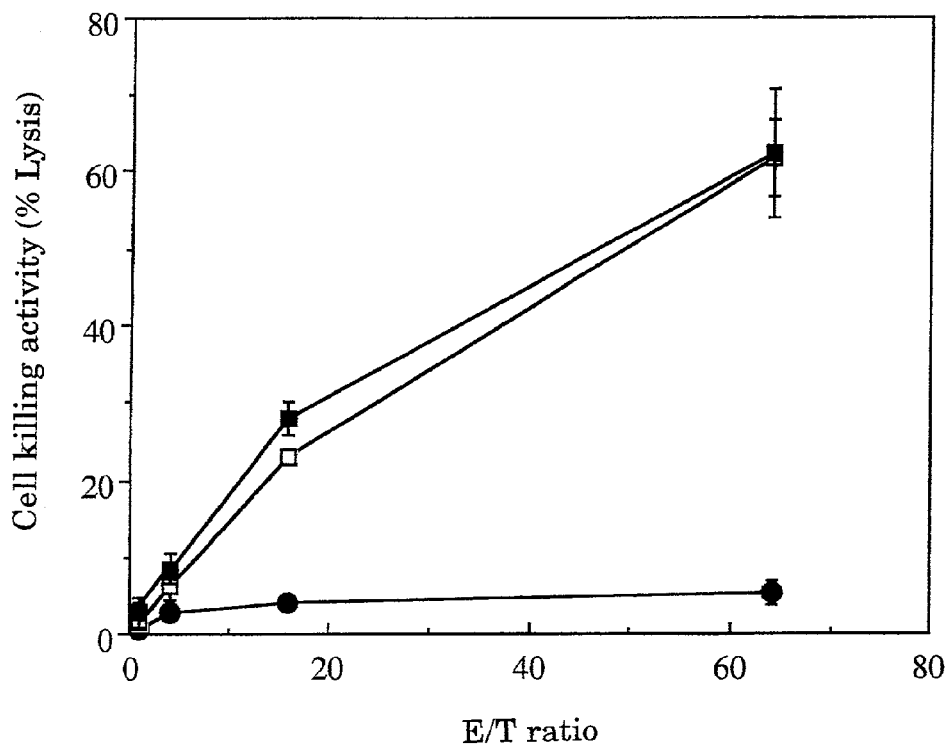
FIG. 3 shows the result of investigation of the cell killing activity by varying the ratio of the cultured lymphocytes and the target tumor cells (E/T ratio). In the figure, ● shows the PBS control group; ■ the group administered with the tumor vaccine; and □ another control group (the group administered with live B16-F10 cells previously irradiated by 50 Gy of X-ray+GM-CSF microspheres).

The cell killing activity was investigated by varying the ratio of the cultured lymphocytes and the target tumor cells (E/T ratio). The results are shown in FIG. 3. In the group treated with the lymphocytes derived from the mice, which were administered with the tumor vaccine preparation in vivo in the same manner as in Example 4, the ratio of the killed target B16-F10 cells was apparently high. The tumor cell killing activity of the lymphocytes was almost equal to the cell killing activity of the lymphocytes derived from another control group (mice administered with the control tumor vaccine preparation) according to the conventional manner which was known to successfully induce CTL. These results suggest that CTL against B16-F1 cells is induced in mice in vivo. In addition, from these results, it is suggested that CTL has a potent tumor cell killing ability, and thus if once CTL is induced, CTL can kill existing tumor cells even in vivo. Accordingly, inhibition of tumor metastasis and cure of a tumor can be expected.

Example 6

CTL Inducing Effect of the Tumor Vaccine Prepared from Solubilized Fixed-Tumor Cells—Using HA-20 Cells

The experiment was conducted to verify that CTLs which can be induced according to the present invention are not solely limited to the CTL against tumor B16-F10 cells used as an antigen.

[Methods]

HA-A20 cells are a B cell lymphoma cell strain derived from Balb/c mice. GM-CSF-HA-A20 cells obtained by altering the HA-A20 cells by genetic engineering are a stable cell strain introduced with expression vectors for two genes of influenza-hemagglutinin and mouse GM-CSF, and have been used as a research material as a classical GM-CSF generative live-cell type tumor vaccine (Levitsky, H. I., et al., J. Immunol., 156, pp. 3858-3865, 1996). A tumor vaccine preparation mixed with 20 μl of the GM-CSF microspheres was prepared by using wild type HA-A20 cells in place of the B16-F10 cells in the same manner as in Example 4, and used for sensitization of Balb/c mice. For the experiment, prepared were the PBS administration group, the group administered with live $10^7$ HA-A20 cells irradiated beforehand with 50 Gy of X-ray, the group administered with a tumor vaccine preparation without mixing the GM-CSF microspheres, and the group administered with live $10^7$ GM-CSF-HA-A20 cells irradiated beforehand with 50 Gy of X-ray as the control groups.

Sensitization of Balb/c mice was carried out by a single administration as in Example 4. Then, the CTL activity against HA-A20 cells was measured in the same manner as in Example 5 using wild type HA-A20 cells in place of the B16-F10 cells. In addition, an experiment was carried out separately in which a monoclonal antibody against mouse CD8 known as a cell surface antigen of typical CTL (Sigma, Product No. F7525, 5 μg) was added to each well of a 96 well plate when measurement was conducted by the 4 hour Cr-51 release method widely known as a standard measuring method.

[Results]

Figure 4:
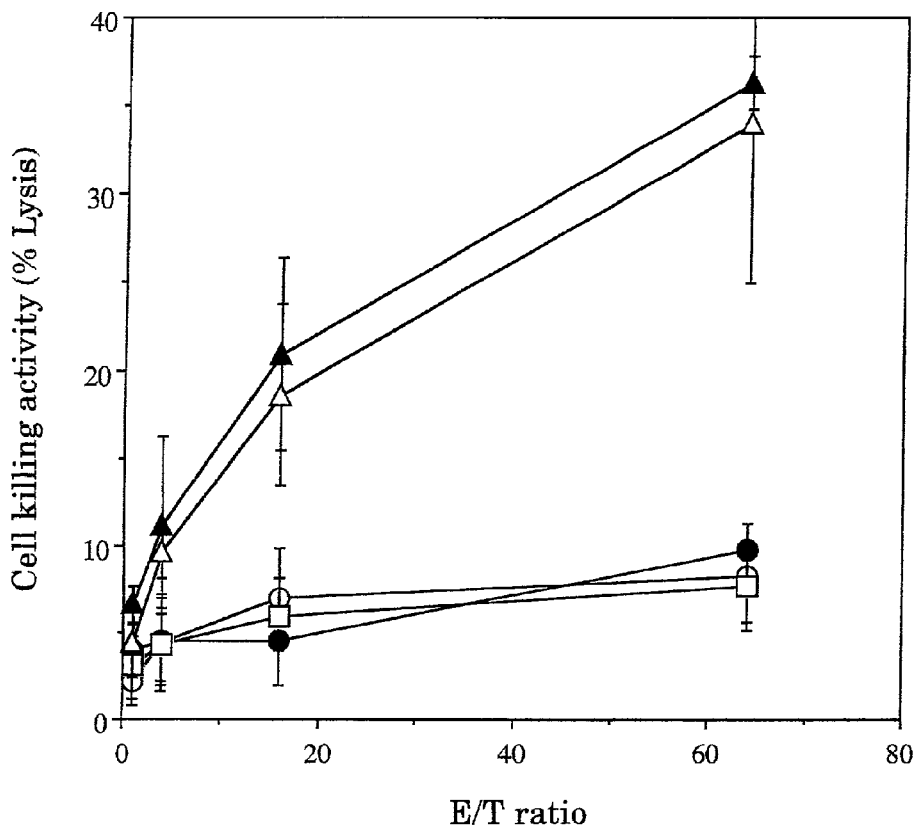
FIG. 4 shows the result of the cell killing activity of each kind of tumor vaccines used in Example 6. In the figure, ● shows the group administered with PBS; ○ the group administered with HA-A20 cells; □ the group administered with the tumor vaccine without being mixed with the GM-CSF microspheres; ▲ the group administered with live GM-CSF-HA-A20 cells irradiated beforehand with 50 Gy of X-ray; and Δ the group administered with the tumor vaccine mixed with GM-CSF microspheres.
Figure 5:
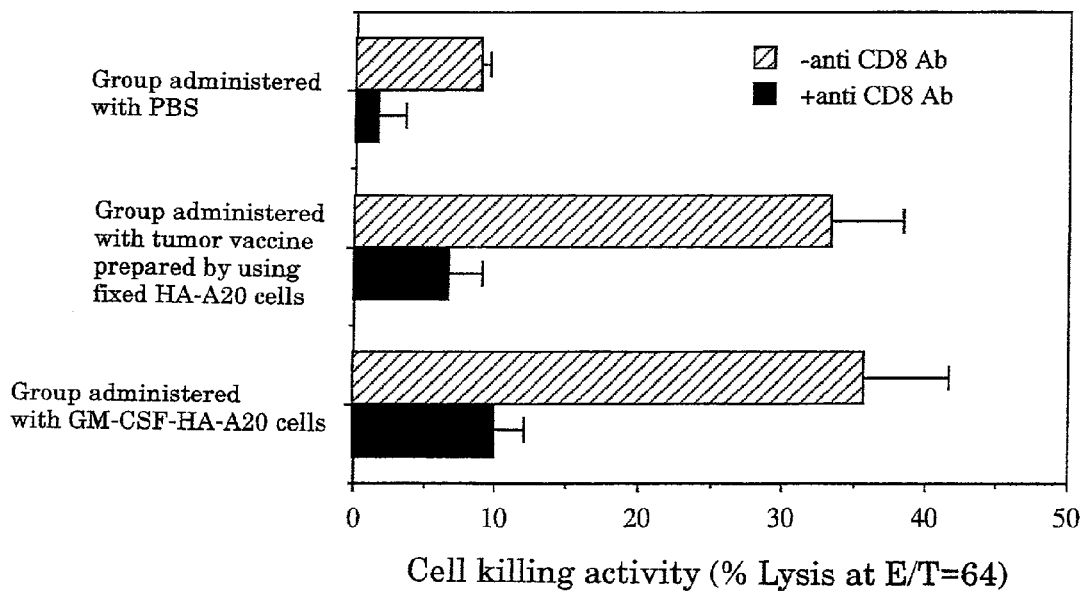
FIG. 5 shows the result of inhibition of cell killing activity of the tumor vaccine of the present invention by a monoclonal antibody against mouse CD8.

As shown in FIG. 4, almost no cell killing activity was observed in the group administered with PBS, the group administered with live HA-A20 cells irradiated beforehand with 50 Gy of X-ray, and the group treated with the tumor vaccine preparation without mixing the GM-CSF microspheres among the control groups. Whilst, in the group administered with the tumor vaccine preparation mixed with 20 μl of the GM-CSF microspheres, apparent killing activity against the target wild type HA-A20 cells was observed, and the potency was almost equal to that in the group administered with live GM-CSF-HA-A20 cells irradiated beforehand with 50 Gy of X-ray which were known as a classical GM-CSF generative live-cell type tumor vaccine. Moreover, when a monoclonal antibody against mouse CD8 was added at the E/T ratio of 64, the cell killing activity was apparently inhibited as shown in FIG. 5. These results suggest that most of the cell killing activity is attributed to CD8 positive lymphocytes, that is a lymphocyte group containing typical CTL.

Example 7

In Vivo Antitumor Effect of Microparticulate Tumor Antigens from the Fixed Tumor Tissues Prepared in Example 2

[Method]

The same experiment as in Table 1 of Example 1 was carried out except that 10 μl in packed volume of the microparticulate tumor antigens prepared in Example 2 were used instead of the $1.25 \times 10^6$ fixed tumor cells used in Example 1 to determine the in vivo antitumor effect. When the cultured live Hepa 1-6 cells were challenged, $2 \times 10^7$ cells were subcutaneously injected into the left thigh in place that $10^7$ cells were directly injected into the liver in Example 1, and the growth rates of tumor tissues were measured exo vivo. The tumor size was expressed as the area of the subcutaneous tumor according to the conventional way in the research filed instead of the volume. A group was also prepared in the above experiment by using 20 μl of commercially available tuberculin (Nippon BCG Production Co.) as an adjuvant instead of 20 μl of Titer Max Gold.

[Results]

As shown in Table 4, the control group formed tumors in all the six mice subjected to the live Hepa 1-6 cell challenge for 3 weeks. However, among the treated groups, in the groups corresponding to Group (B) in Table 1 of Example 1, in which the microparticulate tumor antigens were used instead of the fixed tumor cells, the tumor was formed only in 3 of the 6 mice and the antitumor effect was observed in 3 mice (50%). In the microparticulate tumor antigen group in which the adjuvant was replaced with tuberculin, only one mouse formed tumors and the antitumor effect increased to 83%.

From these results, it was concluded that, as the tumor vaccine to suppress the cancer tissue formation, the combination of the microparticulate tumor antigens prepared from fixed tumor tissues, IL-2 microspheres, GM-CSF microspheres, and Titer Max Gold or tuberculin as an adjuvant was also effective to successfully exhibit antitumor effect.

TABLE 4

| Sensitization | Ratio of tumor-free mice | Tumor volume (mm$^2$) (Mean ± SD) | Range |
|---|---|---|---|
| Control group | | | |
| (A) PBS | 0/6 | 164 ± 76 | 81-256 |
| Treated group | | | |
| (B) Microparticulate tumor antigen from fixed tumor tissues + IL-2/GM-CSF microspheres + Titer Max Gold | 3/6 | 70 ± 80 | 0-180 |
| (C) Microparticulate tumor antigen from fixed tumor tissues + IL-2/GM-CSF microspheres + tuberculin | 5/6 | 8.2 ± 20 | 0-49 |

INDUSTRIAL APPLICABILITY

The tumor vaccine of the present invention can be easily prepared and widely applied for prevention of recurrence, inhibition of metastasis and therapeutic treatment regardless of a type of a tumor. In addition, the vaccine has superior antitumor effect.

What is claimed is:

1. A tumor vaccine comprising:
    (A) a microparticle comprising a fragment of solidified, chemically fixed tumor tissues or cells, said fragment being of a size so as to allow phagocytosis of the fragment; and
    (B) at least one isolated cytokine, at least one isolated compound that is a cytokine-inducing agent, or a combination thereof.

2. The tumor vaccine according to claim 1, which further comprises an adjuvant.

3. The tumor vaccine according to claim 1, which comprises a cytokine-controlled release preparation as the at least one isolated cytokine, at least one isolated compound that is a cytokine-inducing agent, or a combination thereof.

4. The tumor vaccine according to claim 1, which comprises a granulocyte-macrophage-colony stimulating factor, interleukin-2, or a combination thereof, as the at least one isolated cytokine, the at least one isolated compound that is a cytokine-inducing agent, or the combination thereof.

5. A tumor vaccine for use in combination with at least one isolated cytokine, the vaccine comprising, as an active ingredient, a microparticle comprising a fragment of solidified, chemically fixed tumor tissues or cells, said fragment being of a size so as to allow phagocytosis of the fragment.

6. The tumor vaccine according to claim 5, which further comprises an adjuvant.

7. The tumor vaccine according to claim 1, wherein the fragment comprises ground solidified, chemically fixed tumor tissues or cells.

8. The tumor vaccine according to claim 1, wherein the fragment comprises, chemically fixed tumor tissues or cells bound to a particle.

9. The tumor vaccine according to claim 1, wherein the fragment comprises tumor antigen bound to a particle.

10. The tumor vaccine according to claim 7, which comprises a cytokine-controlled release preparation as the at least one isolated cytokine, the at least one isolated compound that is a cytokine-inducing agent, or the combination thereof.

11. The tumor vaccine according to claim 8, which comprises a cytokine-controlled release preparation as the at least one isolated cytokine, the at least one isolated compound that is a cytokine-inducing agent, or the combination thereof.

12. The tumor vaccine according to claim 7, which comprises a granulocyte-macrophage-colony stimulating factor, interleukin-2, or a combination thereof, as the at least one isolated cytokine, the at least one isolated compound that is a cytokine-inducing agent, or the combination thereof.

13. The tumor vaccine according to claim 8, which comprises a granulocyte-macrophage-colony stimulating factor, interleukin-2, or a combination thereof, as the at least one isolated cytokine, the at least one isolated compound that is a cytokine-inducing agent, or the combination thereof.

14. The tumor vaccine according to claim 3, which comprises a granulocyte-macrophage-colony stimulating factor, interleukin-2, or a combination thereof, as the at least one isolated cytokine, the at least one isolated compound that is a cytokine-inducing agent, or the combination thereof.

15. The tumor vaccine according to claim 9, which comprises a cytokine-controlled release preparation as the at least one isolated cytokine, the at least one isolated compound that is a cytokine-inducing agent, or the combination thereof.

16. The tumor vaccine according to claim 15, which comprises a granulocyte-macrophage-colony stimulating factor, interleukin-2, or a combination thereof, as the at least one isolated cytokine, the at least one isolated compound that is a cytokine-inducing agent, or the combination thereof.

17. The tumor vaccine according to claim 10, which comprises a granulocyte-macrophage-colony stimulating factor, interleukin-2, or a combination thereof, as the cytokine at least one isolated cytokine, the at least one isolated compound that is a cytokine-inducing agent, or the combination thereof.

18. The tumor vaccine according to claim 11, which comprises a granulocyte-macrophage-colony stimulating factor, interleukin-2, or a combination thereof, as the at least one isolated cytokine, the least one isolated compound that is a cytokine-inducing agent, or the combination thereof.

* * * * *